United States Patent [19]

Soane

[11] Patent Number: 5,061,336
[45] Date of Patent: Oct. 29, 1991

[54] GEL CASTING METHOD AND APPARATUS

[75] Inventor: David S. Soane, Piedmont, Calif.

[73] Assignee: Soane Technologies, Inc., Livermore, Calif.

[21] Appl. No.: 345,715

[22] Filed: May 1, 1989

[51] Int. Cl.⁵ .......................... G01N 27/40; C08F 2/24
[52] U.S. Cl. .................... 156/245; 156/275.5;
  156/275.7; 156/294; 204/299 R; 264/1.4;
  264/2.3; 264/22; 264/25; 264/319; 522/3
[58] Field of Search ...................... 264/22, 25, 26, 1.4,
  264/2.3, 319; 428/36.5, 36.9, 68, 34.4; 522/3;
  204/299 R; 156/242, 245, 272.2, 275.5, 275.7,
  294, 379.6, 380.9

[56] References Cited

U.S. PATENT DOCUMENTS

| | | | |
|---|---|---|---|
| 3,417,178 | 12/1968 | Downing | 528/323 |
| 4,294,782 | 10/1981 | Froehlig | 522/3 |
| 4,325,794 | 4/1982 | Hunter et al. | 522/3 |
| 4,497,754 | 2/1985 | Padoan | 264/2.3 |
| 4,762,862 | 8/1988 | Yada et al. | 522/3 |
| 4,790,919 | 12/1988 | Baylor, Jr. | 264/22 |
| 4,810,456 | 3/1989 | Bente, III et al. | 204/299 R |
| 4,865,706 | 9/1989 | Karger et al. | 204/299 R |

FOREIGN PATENT DOCUMENTS

| | | | |
|---|---|---|---|
| 0197423 | 10/1986 | European Pat. Off. | 522/3 |
| 0324539A2 | 7/1989 | European Pat. Off. | |

Primary Examiner—Richard V. Fisher
Assistant Examiner—Todd J. Burns
Attorney, Agent, or Firm—Kilpatrick & Cody

[57] ABSTRACT

A gel casting method and apparatus are used to cause a pre-gelled liquid mixture to gel sequentially in a given travelling direction, allowing still-liquid material to flow to the gelling front, replacing volume lost due to shrinkage during the change of state from a liquid to a gel. The differential gelling method provides stress-free gels free of voids common to highly stressed gels, and the method is applicable to column and slab gels, and particularly to capillary columns and very thin slab gels.

9 Claims, 3 Drawing Sheets

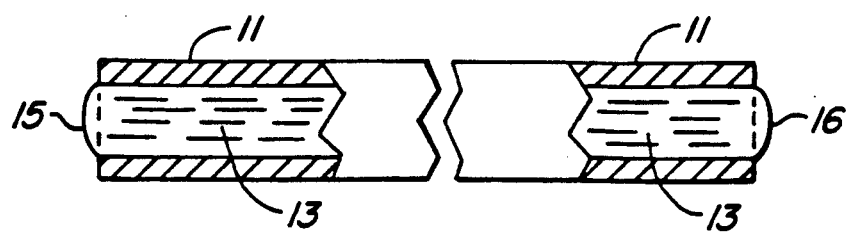
FIG._1A.
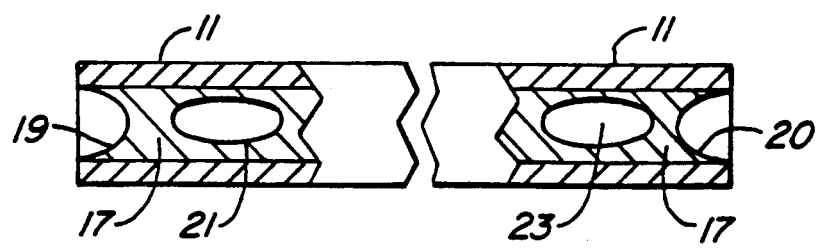
FIG._1B.
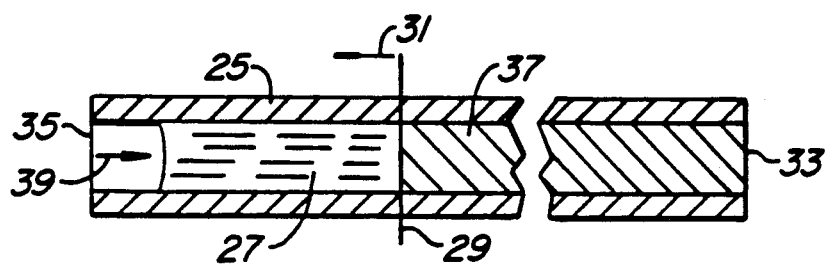
FIG._2A.
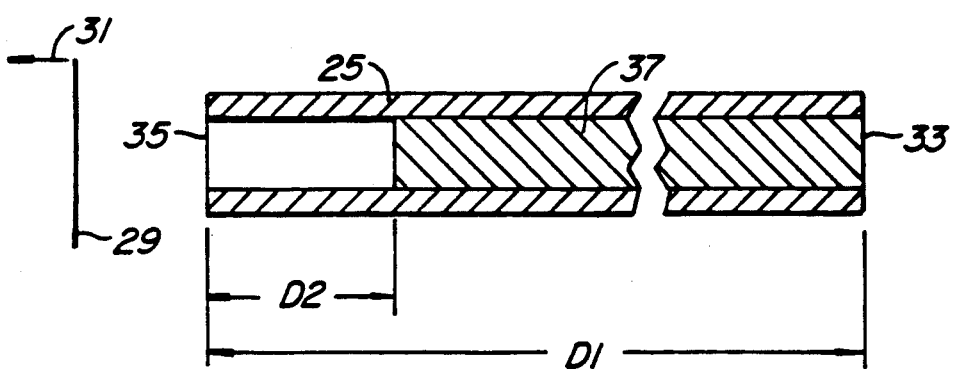
FIG._2B.

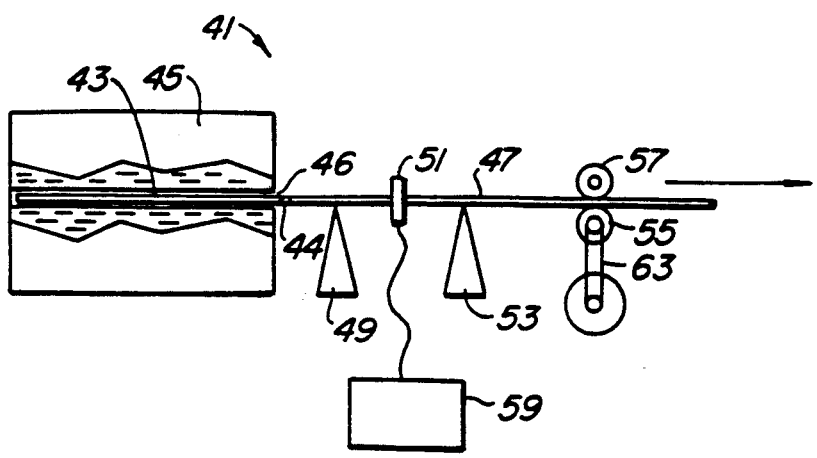
FIG._3A.
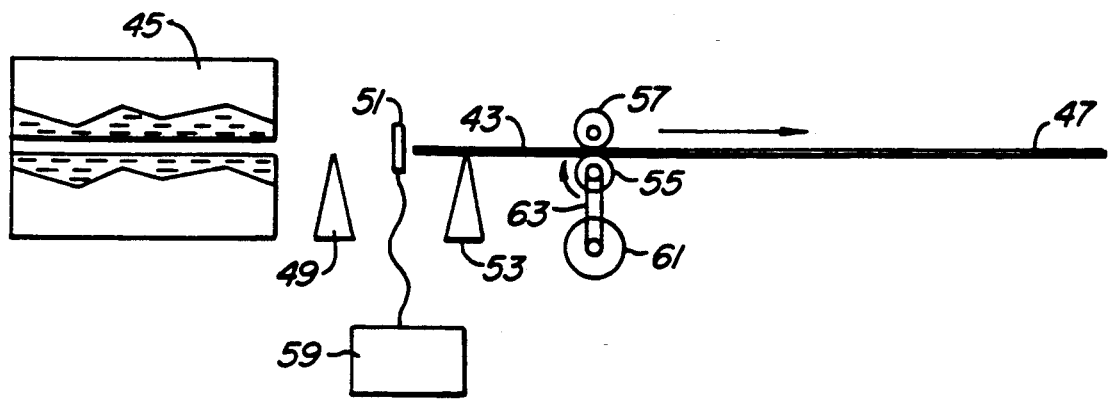
FIG._3B.
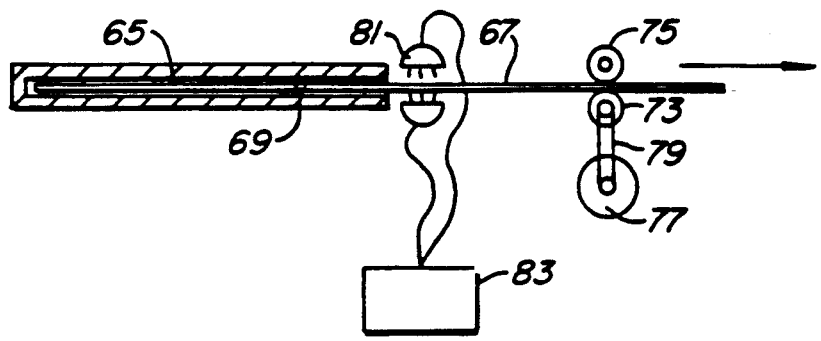
FIG._4.

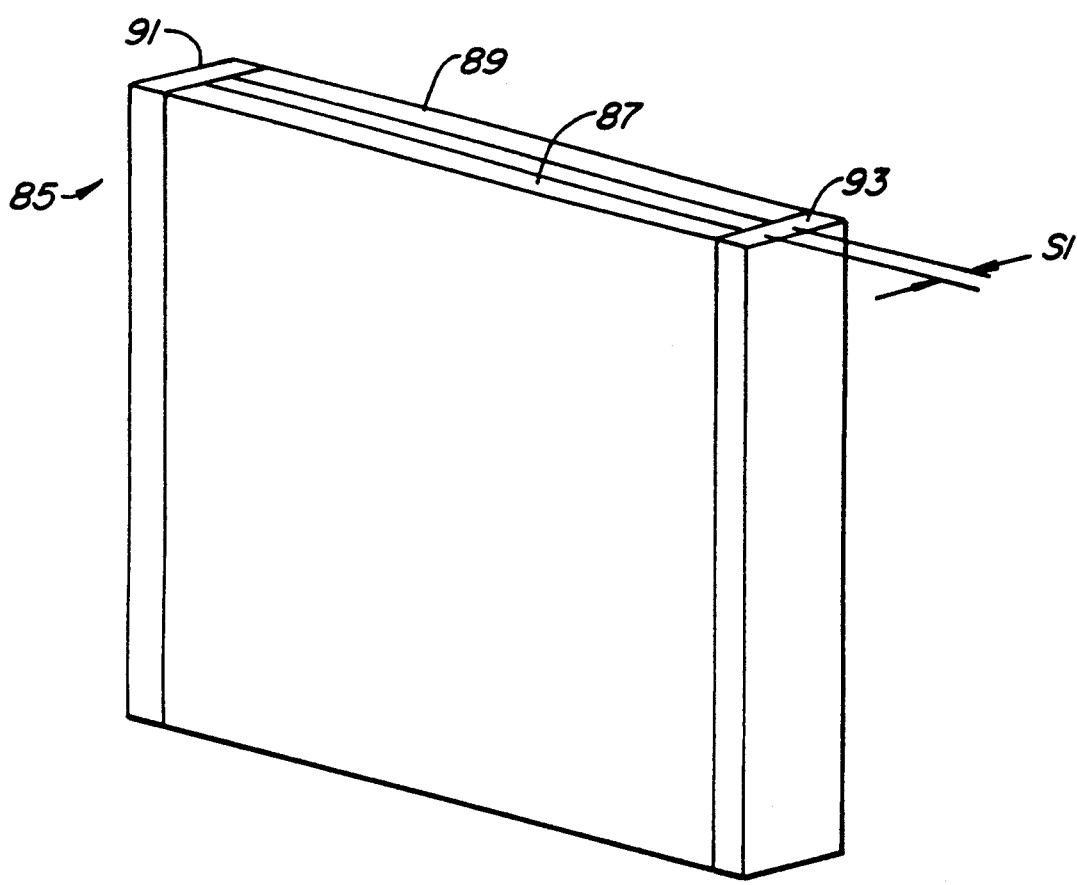
FIG._5.

GEL CASTING METHOD AND APPARATUS

FIELD OF THE INVENTION

The present invention is in the field of gel casting, and relates more particularly to apparatus and methods for casting gels in narrow capillary systems for gel electrophoresis, systems which are particularly suited for use in equipment for analysis and separation of macromolecules such as DNA and proteins.

BACKGROUND OF THE INVENTION

The separation of macromolecules from biological samples by electrophoretic techniques has been a relatively common practice for at least twenty years, and many different devices and techniques have been developed to accomplish various desirable ends. Early techniques involved imposing an electric field across a thin slab of gel and placing a sample of material to be analyzed on one end of the gel. Macromolecules exhibit varying mobility in a properly prepared gel depending on a number of variables, such as an electric charge, size and relative mass of the different species, and shape of the macromolecular species, which may be influenced by a strong electric field. Due to these variations, different species will move into and through a gel at differing rates, forming distinct bands as they move through the gel, thus accomplishing separation. The separate bands are sometimes called fractions, as they are each a portion of the original sample.

After separation is accomplished in a gel, the electric field may be discontinued and the gel removed from any support that is used. There are techniques for rendering the fractions identifiable, such as staining and radioactive tagging, so a spectrum may be recorded. By comparing such spectra with empirical spectra produced from known mixtures and concentrations of such materials, the particular material of each fraction from an experimental sample may be identified. Techniques have also been developed for continuous elution of bands of separated fractions as they move off the end of a gel column.

Gel apparatus may take many different forms in the art, and, in the various different designs, the most common geometries for the gel region are gel slabs and gel columns. These structures are usually prepared by first mixing chemicals, including one or more reacting agents that promote curing of some of the liquid material into a gelled state. A support structure, such as a tube, is then filled with the mixture, and reactions take place to form the gel in the support structure. Typically a starting material is a monomer, one or more of several crosslinking agents, and surfactants. An aqueous buffer is typically included to provide an electrically conductive medium in the gel, compatible with buffers that may be used outside the gel in an electrophoresis system. Other chemicals, such as urea as a denaturing agent, may be included as well. Gels may be of different composition as well, two common compositions being polyacrylamide and agarose, although agarose gels are, in the strict sense, not polymer gels.

In gel electrophoresis, the gel is commonly cast in an aqueous solution including an ionic buffer, and an electrical potential is applied across the gel. The electrical potential is responsible for the force causing molecules to migrate through a gel, and also induces an electric current. The passage of the electric current in traditional systems, with gel slabs and columns having thicknesses and diameters of several millimeters and greater, has been a problem in many instances due to Joule heating. Such heating, for example, can cause distortion of the gel structure and subsequent interference with the separation process. To overcome the Joule heating effects, electrophoresis apparatus is often complicated and bulky, including elaborate elements and structures for removing heat.

The heating problem has led in the art to construction of apparatus with smaller and smaller gel structures. At the present time, the industry is headed toward the use of very thin slabs and rectangular and cylindrical capillaries filled with gel. In principle, the thin-wall and small diameter structures should prove very effective as the surface area of the supporting structures relative to the bulk of the gel is larger than in traditional structures. Although the heat per unit volume generated would be the same, the heat transfer away from the gel should be facilitated. In these thin structures, the preferred thickness of slabs and diameter of capillaries would be in the range of from tens to hundreds of microns. A number of recent publications discuss the relative merits of capillaries of narrow dimensions for gel electrophoresis, for example, see A. S. Cohen and B. L. Karger, J. Chromatography, 397, 409 (1987); and S. Hjerten, et al., J. Chromatography, 403, 47 (1987).

The usefulness of a cast gel for biomedical separation procedures depends upon a number of variables. The relative degree of crosslinking is important to the migration of macromolecules, for instance, and the homogeneity of the gel may be important. In many cases, the gel must be firmly adhered to the walls of the support structure, typically glass or plastic, so that the gel material does not migrate in the system due to electroendosmosis. Some work has been performed in this area as reported in Hjerten et al. (ibid), which described the importance of wall treatments in suppressing adsorption of sample solutes onto the walls. Such coatings included for example, methylcellulose or linear polyacrylamide.

The gel must be continuous, too. The appearance of voids, particularly with capillaries of small overall diameter or thickness, can render a gel structure useless. A void can cause an anomaly in the continuity of the electrical circuit, or may seriously alter the nature of macromolecular bands as they migrate. The appearance of such voids has been a particularly vexatious problem in the preparation of such gels in capillary systems, despite the fact that extensive fundamental research concerning the polymerization kinetics and product gel behavior has been reported in the literature. (See, for example, A. Chrambach and C. Rodbard, Separation Science, 7, 213 (1981); C. Gelfi and PlG. Righetti, Electrophoresis, 2, 213 and 220 (1981); and P. G. Righetti, et al, Electrophoresis, 2, 291 (1981).)

All of these problems, however, need to be overcome in the casting of gel structures. What is needed is an apparatus and method for preparing gel structures that is reliable, in which the degree of crosslinking can be controlled, and most importantly that results in structures without voids.

SUMMARY OF THE INVENTION

In accordance with the preferred embodiments of the present invention, a method and apparatus are presented for the casting of gels with substantially reduced stress, without voids, in confined support structures, particularly in narrow bore capillaries and in thin slab-type configurations. In the preferred mode, the support structure for containing the gel has a wall constructed of a material that transmits energy.

According to the method, the steps for casting the gel include filling the support structure with a mixture containing a gelling material so that the mixture is continuous from a first location to a second location in the support structure. Then the gelling mixture is sequentially polymerized from the first location to the second location.

In the preferred mode, the support structure has a wall that transmits energy and the mixture is promoted to gel by absorption of energy. After the support structure is filled, energy is provided to a localized area at the position of the wall. The support structure and the energy source are then moved relative to each other so that the localized area that receives energy from the source is moved along the wall in a direction from the first location toward the second location on the wall, thereby causing gellation to occur in the gelling mixture in a moving zone substantially adjacent to the localized area as the localized area moves.

In the preferred mode, the gel is primarily polyacrylamide, crosslinked by any of a number of crosslinking agents. Also the gel can be cast in aqueous solutions loaded with a selection of buffers (e.g. Tris phosphate or borate), surfactants, and other functional chemicals useful in biomolecule separations. In the preferred mode, the cast gel is firmly covalently bonded to the walls of the support structure by surface coupling agents.

The method relies on sequential polymerization of differential slices of the pre-gel mixture. Hence, adjacent regions of the pre-gel mixture are caused to polymerize successively, beginning at the first location on the wall of the support structure and ending at the second location on the wall of the support structure, until the entire mixture therebetween has gelled. The unpolymerized or slightly polymerized section of the support structure during this differential casting process is filled with a low viscosity, highly mobile liquid. Contraction due to the polymerized and polymerizing portions is then compensated by the gradual inflow of the low viscosity material, replenishing the volume lost due to contraction. The tethering reaction through coupling with the wall coating agent occurs simultaneously as the gelling front moves down the lenth of the tube.

In the preferred embodiments, two approaches are presented in detail for this differential activation process. In the first implementation, polymerization is initiated thermally, e.g. by free radical decomposition of a peroxy compound such as persulfate (ammonium or potassium persulfate) using an accelerator. In the preferred mode, the regions of the support structure that have not yet been exposed to the thermal gradient are kept cold, keeping the unpolymerized reaction mixture in a mobile state. Upon warming, reaction occurs rapidly, leading to gellation (and accompanying contraction). The rate of the motion of the thermal front is controlled, so that migration of the low-conversion material from the cold section can keep pace with the demands of volume replacement caused by contraction.

In the second implementation, the reaction mixture includes a photoinitiated activator, e.g. riboflavin, rather than using a thermal activation process. The energy source then includes a source of electromagnetic radiation having the frequency required for photoactivation. As in the previous embodiment, the source and support structure are moved relative to one another to accomplish the differential activation process.

BRIEF DESCRIPTION OF THE DRAWINGS

FIG. 1A is a cross-section of a capillary tube filled with a liquid to be gelled.

FIG. 1B is a cross-section of the tube of FIG. 1A after gelling of the liquid mixture.

FIG. 2A is a cross-section of a capillary tubing with gellation occuring at a moving front.

FIG. 2B is a cross-section of the tube of FIG. 2A after gellation is complete.

FIG. 3A shows an apparatus for gelling liquid mixture in a support structure by heat application before processing starts.

FIG. 3B shows the apparatus of FIG. 3A after processing.

FIG. 4 shows an apparatus for gelling liquid mixture in a support structure by ultraviolet radiation.

FIG. 5 shows a support structure for casting a slab gel.

DESCRIPTION OF THE PREFERRED EMBODIMENTS

As indicated earlier, among the problems that are commonly encountered in the casting of gel structures, particularly in micro structures such as capillary apparatus that have a high surface area to volume ratio, the appearance of voids has been of particular concern. It has been thought by many that voids that appear in the casting procedure were the result of outgassing of entrained gases in the liquid mixtures, and consequently, apparatus and procedures have been incorporated for outgassing the mixtures before and during curing to remove any such dissolved or entrained gases. Also it has been thought that gases are formed during the polymerization reactions. Such apparatus for outgassing is often expensive, incorporating vacuum pumps and vessels, and the procedures are time consuming and costly. In investigations leading to the present invention, it was found that bubble-like voids appearing in the process of gel casting were not outgassing inducedvoids, but most usually are voids caused by shrinkage of material in the gellation process. Relatively simple analytical techniques, such as measuring the weight and volume of a liquid mixture before gelling, and the weight and volume of the same mixture after gelling occurs, shows that there is significant shrinkage as a result of the polymerization that takes place, e.g. 20% or higher for a pure gel and 2% for a 10% gel. Shrinkage of the material, particularly if the material is adhered to the walls of a capillary or other tubing or surface, causes large tensile stresses, which, if large enough, will cause voids to appear. The resulting voids relieve the tension in the gelled material.

FIG. 1A is a side view, partially sectioned, of a capillary tubing 11 which has been filled with a liquid mixture 13 of materials including a gelling agent that will cause a primary component of the mixture to gel. Initially, the liquid fills the tube, with a small miniscus 15 and 16 at each end of the tube. The volume of the liquid is substantially the volume of the internal bore of the capillary (ignoring the miniscus), this being the area of the bore times the length of the tubing.

FIG. 1B shows the same tubing at a later time after the liquid mixture has gelled. Gel 17 is shown then with the crosshatching of a solid material (although a gel is a considerably flexible substance). Shrinkage takes place in the gelling process, so gel 17 will occupy less volume than the original liquid, unless sufficiently constrained from so doing. There is, indeed, one such constraint. The gel has adhered to the walls of the bore of the capillary.

In this example, all of the material was gelled at substantially the same time, and the adhesion to the wall occurred at the time of gelling. As the material gelled, and consequently shrank, the material at the wall could not move relative to the wall, and that material formed flexible bonds with adjacent material. The material at the wall is therefore relatively more highly stressed than the material further from the wall, and the material near the center of the bore, having the most freedom of movement, is the least stressed. Part of the relief of stress for the material near the center is the result of the fact that there are no end restraints, so the gelled material at the ends of the tube will take the inverted form shown approximately by end profiles 19 and 20.

In a very short tube, and in tubes of relatively large diameter, the end movement may be the only form of stress relief in the process. In capillary tubes, however, the length to diameter ratio is very high, and the end movement can only compensate for a very small amount of the total volume shrinkage that would be required to relieve the stress. If the percentage of volume shrinkage in an unrestrained system were 5%, for example, the end movement would have to be 5% of the total bore volume to produce an unstressed gel. In the typical case, however, the end movement in capillary tubes is much less than that required to accommodate the shrinkage volume, so either the resulting gel is highly stressed, or another stress relief mechanism appears.

In general, the result is that the stress in the gel overcomes the cohesion between molecules of material, and voids appear, voids which look very much as bubbles would look if gas were to evolve in the material as gelling takes place. Voids 21 and 23 shown in FIG. 1B illustrate the results of this tearing effect. The voids typically appear as gelling proceeds, rather than at a later time. This is believed to take place because the gel gains in tensile strength as polymerization proceeds, the higher tensile strength being able to support a higher tensile stress without tearing to form voids. It is true, too, that the formation of voids in this fashion does not entirely relieve the stress, as the voids only form if the stress becomes larger than the tensile strength of the material at the time of formation of the void.

In the present invention, liquid systems in capillaries and between plates for slab-type systems are caused to gel in a differential fashion along a moving front, so that material ahead of the moving gel zone remains liquid, and material that the front has passed is gelled. The still-liquid material ahead of the moving gel zone may then flow to that zone, at a rate that equals the rate of shrinkage, and a void-free, stress-free gel is produced.

FIG. 2A shows a capillary tube 25 similar to that shown in FIG. 1A. The tube of FIG. 2A was initially filled with a liquid mixture 27 similar to the liquid mixture that filled the tube in FIG. 1A, so that the mixture was continuous and filled the tube from a first point to a second point along the wall of the tube, in this case from one end to the other. The capillary is shown as broken to indicate that the length is much greater than the diameter. A typical length for a capillary for a gel electrophoresis apparatus is 15 cm., and a typical bore is 100 microns.

In the system represented by FIG. 2A, the liquid mixture does not gel all at substantially the same time. Rather, gelling occurs at a thin moving front, represented by plane 29, moving in the direction of arrow 31. The gelling front starts at one end of the liquid filled capillary, in this instance end 33, and proceeds at a predetermined velocity to the other end 35. As the gelling front passes, the liquid material gels, and material 37 "behind" the gelling front is gelled material. Adhesion to the inside wall of the capillary occurs at substantially the same time that gelling occurs.

The fact that gelling takes place with shrinkage dictates that liquid material 27 "ahead" of the moving front must flow toward the front, in the direction of arrow 39, to make up for the volume loss. The fact that the material ahead of the front remains liquid allows the flow to take place, thus relieving stress so as to eliminate the bubble-like voids that are evident when the liquid material gels all at the same time.

FIG. 2B represents the condition of the capillary of FIG. 2A after the gelling front has passed the full length of the tubing. All of the liquid mixture has been gelled, and the space unfilled at the end of the tube where gelling last took place, represented by length D2, is the volume contraction due to the gelling process. The ratio of D2 to the length of the tubing D1, which was originally filled with the liquid mixture, will be the same as the fractional contraction in the gelling process. That is, if a mixture is provided that contracts 3% in gellation, then D2 will be substantially 3% of D1, if one does not keep the end of the capillary in contact with a reservoir of gelling mixture during the zone gellation process.

One way that gelling may be caused to occur at a moving front is by using a liquid mixture in which the rate of gellation is a function of temperature. A length of capillary or the space between two flat surfaces is filled with the mixture, and the support structure filled with liquid mixture is kept at a reduced temperature, such as by immersion in an ice bath, until processing commences. The support structure is then drawn through a heated zone so that gellation takes place at a moving front substantially in the manner illustrated in FIGS. 3A and 3B. In practice the heated zone is typically about 2.5 cm to 5 cm (1 in. to 2 in.) in length since that is a convenient size for a resistance heater. It should be understood, however, that other lengths could also be used for the heated zone, either longer or shorter. All that is required is that the gellation zone not be so long that shrinkage cannot be compensated for as the zone is moved along the length of the tube.

FIG. 3A depicts an apparatus 41 as a preferred embodiment of the invention in which heat is used to induce gelling of a liquid mixture at a moving front. A length of capillary tubing 43 is filled with a liquid mixture in which gelling rate is a function of temperature. In the typical case, capillaries of fused silica or glass are used, with bore diameters from 10 microns to 1000 microns, although plastic capillaries could be used as well, and the concept of the invention does not appear to be restricted to a particular bore size. An example of a mixture that works well in the apparatus and with the method described is as follows:

(1) Monomer: Acrylamide (10% w/v i.e. 10 gms/100 ml)
(2) Comonomer/Crosslinker: N,N'-methylenebisacrylamide (Bis, 3% w/total solid weight)
(3) Initiator: Ammonium persulfate (0.05% w/v)

(4) Coinitiator/Accelerator: N,N,N',N'-tetramethylethylene-diamine (TEMED, 0.06% v/v, i.e. 0.0006 ml/ml)
(5) Surfactant: Sodium dodecylsulfate (SDS, 0.1% w/v)
(6) Buffer: Tris/Phosphate (0.1M)
(7) Modifier: Urea (7M).

For this exemplary mixture, a 100 micron fused silica capillary was used, with a heated zone temperature of 43 Degrees C., a pulling rate of 0.8 cm/min. and a 5 cm (2 in) heated zone length.

Those skilled in the art will appreciate that the concept of the invention is not restricted to the particular compounds described above to form the pre-gel mixture. Generally any monomer can be used which shrinks on polymerization. Hence, as a minimum set, all that is needed is a monomer and an activator to activate the monomer to cause chain lengthening, either by step process or addition. In this example, the activator is the initiator which breaks the double bonds of the monomer, a process that characterizes those monomers that can be polymerized by means of free-radical initiation. In this embodiment, the free-radical initiation is caused by a thermal decomposition initiator. For separation of biomolecules using gel electrophoresis, aqueous soluble vinyl monomers are particularly useful, other examples including acrylic acid, methacrylic acid, vinyl alcohol, vinyl acetate, methacrylamide, 2-oxazolines, and pyrrolidone derivatives such as vinyl or methyl pyrrolidone. For the acrylamide monomer of the preferred embodiment and these aqueous soluble monomers, a typical concentration is in the range of 3 to 20% w/v. For other monomers such as latex, a typical concentration of monomer can be as high as 50% w/v. (In the preferred mode example above 10% w/v was chosen based on the type of biomolecules that were contained in the sample that was to be separated). Other solvents may also be used, for example, methanol and acetonitrile. Similarly, some non-aqueous soluble monomers would include styrene, methyl methacrylate, and silanes.

In general, the basic structure of the gel is determined by the monomer. Hence, in this application, as in others which use polymer gels, a comonomer or crosslinker is typically used to change the basic structure of the gel, depending on the nature of the molecules to be separated. For polyacrylamide gels, other well-known crosslinking agents are also effective, such as N,N'-bisacrylylcystamine (BAC), N,N'-diallyltartardiamine (DATD), N,N'-(1,2-dihydroxyethylene) bisacrylamide (DHEBA), ethylene diacrylate (EDA), and others. For all of these crosslinkers, a typical range of concentrations is from 2 to 5% weight/total solid weight. Those skilled in the art will understand that other concentrations may be used depending on the desired structure and the nature of the separation to be performed.

Other initiators may also be used, provided they are appropriate for the monomer/crosslinker combination used. For the above combinations, for example, potassium persulfate may be substituted for ammonium persulfate as an initiator. In general, however, the classes of compounds that are useful as thermal decomposition initiators for general polymerization reactions are somewhat limited and other classes that are typically used are those with O—O, S—S, or N—O bonds, since these classes of compounds exhibit bond dissociation energies in the range of 100–170 kJ/mole. Compounds with higher or lower bond dissociation energies will typically dissociate too slowly or too rapidly. A notable exception to this general rule are some azo compounds, such as 2,2'-Azobisisobutyronitrile (AIBN), which has a dissociation energy of the N=N bond of about 290 kJ/mole, but the driving force for homolysis there is the formation of the highly stable nitrogen molecule. It is expected that these compounds would behave similarly when used for polymer gel formation for separation purposes. For the more general polymer systems where thermally initiated polymerization is used, the peroxides have typically been the initiator of choice (e.g. acyl peroxides such as acetyl and benzoyl peroxides, alkyl peroxides such as cumyl and t-butyl peroxides, hydroperoxides such a t-butyl and cumyl hydro- peroxides, and peresters such as t-butyl perbenzoate).

Similarly, other accelerators may be used as catalysts for the crosslinking, particularly those that will cause the crosslinking reaction to become a stronger function of temperature. The use of crosslinkers tends to make gel much more stable during use as well as contributing to the establishment of an effective pore size for the gel. There is also a broad range of soap-like molecules that will serve well as surfactants, such as Triton-x, Tween-x, and Brij-x. These surface modifiers are used to change the nature of the interaction of the biomolecules with water, with each other, with their environment, since these molecules are often hydrophobic and tend to stick together in aqueous solutions. The surfactants help separate the solute into individual molecules which can then migrate individually down the gel. Similarly, other appropriate buffers may be used for pH stabilization, or they may be used for control of ionic strength, since some molecules tend to bind to particular ions. Some examples of other buffers include borates, phosphates, citrates, carbonates, etc.

Various modifiers may also be used which generally are dependent on the type of molecule being analyzed, and on how the interaction of the solute with the other compounds in the gel matrix is to be altered. In the example given, the purpose of the Urea is to weaken intramolecular hydrogen bonding, which helps to ensure denaturation of any protein solutes injected into the capillary. As a general rule, if it is not anticipated that biomolecules are to be separated, Urea is unnecessary, and even there separations can often be effected without it. Another useful modifier for biomolecular separations is guanadine, typically about 5M, which is sometimes used in combination with Urea. Those skilled in the art will appreciate that there are many other useful modifiers which can be used to control or change the nature of the separation process. For example, other useful modifiers include alcohol, and acetonitrile.

The use of a wall coupling agent has been found to significantly enhance the stability of the gels produced, since the gels are then held firmly in place by the wall. Use of such wall couplings is a common practice in the art. An additional benefit of the present invention, however, is the simplicity of the preferred wall coupling procedure used. In particular, prior to filling the capillary with the mixture of materials above which will form the gel, straight (pure) or diluted 3-methacryloxypropyltrimethoxysilane (MAPTMS) (in acetone solution) is used to coat the capillary. The capillary is then air dried and heated in an oven for three hours at about 130 degrees Centigrade to effect MAPTMS binding to the capillary wall surfaces. The MAPTMS promotes strong wall adhesion and a dense, highly cross-linked gel adjacent to the wall. Although not as simple, other wall coupling agents and procedures may also be used. For example, another approach is to covalently bond aminopropyltrimethoxysilane or aminopropyltriethoxysilane to the wall. N-acryloxysuccimide is then used to cause substitution addition. This is then followed by treatment with diethylacrylamide to cause crosslinking of the materials on the wall. In all of the procedures above, the goal is to leave a wall surface covered with double bonds directly linked to the wall by chemical bonds. These double bonds can then react with acrylamide monomers and crosslinkers in the differential gellation process.

Once the wall is treated, the capillary can then be filled with the gelling mixture, and the casting process begun. In the preferred mode, the liquid mixture of the material to be gelled in the capillary is kept at ice bath temperature (0 degrees Centigrade) during preparation (not shown) and during injection into capillary 43 (also not shown). Injection can be by pressure apparatus, such as a syringe, or by other methods of creating a pressure differential, such as creating a vacuum at one end of the capillary with the other end immersed in the liquid mixture. Once the tubing is filled, it is placed in a cold chamber 45 through an opening 46 in the chamber.

A leader 47 is attached to the capillary to serve as an attachment for pulling the capillary out of the cold chamber once the process is initiated. The leader may be a length of unfilled capillary or solid rod of substantially the same outside diameter as the capillary, and there are several appropriate ways of attaching the leader to the capillary, such as a short piece of flexible tubing over the outside diameter, or a short piece of flexible rod in the inside diameter. In the illustrated embodiment the attachment point is point 44 between the leader and the capillary. Alternatively, a longer piece of capillary may be used without a leader.

In the preferred embodiment, leader 47 passes over a support slide 49, through an activating system 51, over a second support slide 53, and into a set of rollers comprising a propulsion roller 55 and an idler roller 57. The propulsion roller is driven by an electric motor 61 through a belt 63. In the preferred mode, the motor has a speed control (not shown).

In the preferred embodiment, the activating system 51 is a heat ring which has a resistance heater, and an electrical controller 59 is connected to the heat ring. Other activating systems could also be used for heat-activated gellation, for example, a ring of thermostatically controlled fluid, heated by a resistance heater is also convenient, or a laser could also be used. Also, for embodiments which do not use heat-activated gellation, the activating system 51 could be an optical system or a laser if the gellation is photoactivated, or even a beam of ionizing radiation if the gellation is activated by such radiation.

Once all the preparatory steps are made, the heat ring is brought up to temperature, and the propulsion drive is started. The liquid-filled capillary is drawn out of the cold chamber and through the heat zone. The liquid material in capillary 43 is gelled along a moving front, as described above with reference to FIG. 2A and FIG. 2B., and the still-liquid material in the capillary flows toward the reaction (gelling) plane, making up for the volume shrinkage due to gellation. FIG. 3B shows the capillary drawn fully through the heat ring, and the gelling process in the capillary is complete.

As indicated earlier, the temperature of the heat ring is controlled, the temperature used being determined empirically, and generally depends on the composition of the liquid material, the distance of the ring from the capillary, the material, bore, and wall thickness of the capillary, and the rate at which the capillary is drawn through the heated zone. In the preferred embodiment described, a temperature of about 43 degrees C. was used. In other situations temperatures as low as 30 degrees have been successful, and the preferred range of temperatures appears to be about 25 to 50 degrees C.

The rate at which the tube may be drawn is controlled as well. Since the capillaries used are of small bore, 20 to 500 microns, they present a significant restriction to flow, and if the pulling speed is too high, the liquid flow will not be able to compensate for the shrinkage. The volumetric flow rate due to shrinkage is the product of the percentage actual shrinkage, the cross-sectional area of the tube, and the pulling velocity, and is relatively easily calculated. The ability of the liquid to flow through the tube to the moving front at a rate high enough to replace the shrinkage volume is related to the pressure differential from the open end of the tube to the gelling front. The pressure differential may be calculated by well known fluid flow equations, and is directly proportional to the product of the viscosity, the tube length for the flowing liquid, and the volumetric flow rate, and is inversely proportional to the fourth power of the radius of the tube. Hence, as the tube diameter becomes small, as for capillary systems, it is important to keep the viscosity of the flowing material low enough so that the mixture can flow sufficiently well to replace the volume lost due to shrinkage during gellation. Operationally, for the particular mixture chosen in the above example, this means that the temperature of the mixture in the un-reacted portion of the capillary should be maintained well below the reaction temperature for gellation, before it is introduced into the heated reaction zone. In practical terms, this is accomplished by the ice bath for the preferred mixture described. However, for other combinations of materials and reaction temperatures, such temperatures may be better maintained by temperature controlled refrigeration systems, or may not need to be controlled other than by the ambient atmosphere if the reaction temperature is high enough and the reaction zone heater is well enough confined. Also, it is apparent that the pressure differential may be increased by pressurizing the fluid in the cold end of the tube.

In the preferred embodiment with the mixture described and the cold zone maintained at 0 degrees C. (ice), with a glass capillary of bore radius 0.005 cm., the pulling speed could be maintained at about 1 cm. per minute, while relying on atmospheric pressure as one limit of the pressure differential across the liquid portion of the mixture.

As indicated earlier, the use of a heat-sensitive mixture and the application of heat at a narrow region while providing relative movement between the tubing and the heat zone is just one way of creating a moving gelling front. In an alternative preferred embodiment, a liquid mixture is prepared having a gelling rate that is a strong function of exposure to electromagnetic radiation. In this embodiment, the polymerization is photoinitiated. Generally photoinitiation occurs when light absorption results in the production of radicals, typically by one of two pathways: a) one or more compounds in the system undergo excitation by energy absorption, ie. electronic transition, and subsequent decomposition into radicals, and/or b) one or more compounds undergo excitation and the excited species interacts with a second compound (by either energy transfer or redox reaction) to form radicals derived from the latter and/or former compound (s). To accommodate this photoinitiated process, the mixture is similar to the mixture described above for thermally initiated polymerization, except a photoinitiator, such as riboflavin which absorbs light in the ultraviolet portion of the spectrum, is used instead of initiators and accelerators that are temperature sensitive. Other aqueous photoinitiators that may be used are also well known in the art, and include azo-dicarbonamide, 1,1'-azobis (N,N-dimethylformamide), and sodium salts of 4,4'-azobis (4-cyanovaleric acid).

As a specific example of a mixture which can be used for a photoinitiated process, the set of ingredients would be the same as for the example of a thermally initiated mixture above and equivalents thereof as discussed, except for the substitution of riboflavin for the initiator. In the preferred mode, the riboflavin is used at a concentration of 0.005 mg/ml, and can generally be varied from 0.0005 mg/ml to 0.04 mg/ml, or even higher, and similarly for the other photoinitiators described above.

FIG. 4 shows an apparatus, similar to the apparatus for heat initiated reaction, for use with a photosensitive mixture. A capillary 65 is filled with a liquid mixture similar to the mixture described for a heat initiated reaction, except the initiator is photosensitive. Preparation is done in the absence of ultraviolet exposure, and after mixing and filling, the tube is attached to a leader 67 at interface 69. Coating with MAPTMS inside the bore is typically done, as with the first described preferred embodiment, to promote wall adhesion. The filled capillary is placed in a shroud 65 to prevent exposure to ultraviolet, which would initiate polymerization and crosslinking. Leader 67 passes between a driven propulsion roller 73 and an idler roller 75. Roller 73 is driven by an electric motor 77 through a belt 79. An ultraviolet exposure zone 81 comprises ultraviolet lamps driven by a power supply 83. In operation the lamps are turned on, the motor is started, and the liquid filled tube is drawn through the exposure zone at a controlled velocity. Gelling occurs at a moving front relative to the length of the capillary, substantially at the exposure zone, and still-liquid material in the capillary portion that hasn't passed through the gelling zone flows in the capillary to replace the volume lost due to shrinkage.

A substantial difference in the heat initiated and the photoinitiated processes is in the initiation and the chemicals added to the mixtures to provide heat sensitivity or photosensitivity. The same flow and pressure relationships limiting the pulling rate hold in either case. There is a significant advantage in the photoinitiated case, in that the unexposed mixture does not gel in the dark, unlike the refrigerated mixture, in which the gelling rate is depressed. This provides a long shelf life for the liquid mixture prior to exposure, which is an advantage for commercial production. In addition, photoinitiation provides a sharp "on/off" switch for the gellation process, unlike thermal activation which is harder to control.

The limitations relative to capillary bore diameter and tube length that severely limit the useful and effective pulling rate are a clear disadvantage for commercial production purposes. These limitations may be overcome significantly by providing an elevated pressure at the end of the liquid-filled capillary that is the last to pass through the gelling zone, rather than relying on atmospheric pressure. This increases the pressure differential and allows a higher pulling rate to be employed than would otherwise be effective without incurring cavitation at the gel/solution interface. Typically, the pressure should be high enough at the start of the process that the pressure at the gel/solution interface is about 1 atmosphere ($1 \times 10^6$ dynes/cm$^2$). The elevated pressure may be supplied by a syringe, by attaching a flexible tubing and pressurizing with a gas like nitrogen, or by other kinds of apparatus. In case of pressurization, the opposite end of the liquid-filled capillary is stoppered (closed) to prevent the pressure from forcing the liquid out that end before polymerization and wall adhesion commence. Such a pressure assist is especially important for long capillaries. Pressure calculations based on well known fluid flow equations indicate that for a bore of 0.005 cm and a length of 100 cm, a pressure of about 20 PSI ($1.3 \times 10^6$ dynes/cm$^2$) is indicated.

The gelling of mixtures along a moving front is not limited to round bore capillaries, but is useful as well for casting thin capillaries of rectangular cross section, ie. slab structures. Such a slab structure is illustrated in FIG. 5 which shows a support structure 85 comprising plates 87 and 89, and edge seals 91 and 93. The figure is not to scale, and the spacing S1 between the plates has been exaggerated for purposes of illustration. The spacing S1, in the preferred mode, is about 100 microns, so that a very thin slab gel may be cast between the plates. Furthermore, in some instances, the spacing may be even smaller, say 50 microns, or even as small as 25 microns, although at such small spacings it is more difficult to keep the apparatus dimensionally stable. Other larger spacings may be also used, for example as large as 500 microns. However, as the spacing gets larger, the invention is generally not as important, since at some point there is sufficient distance between the plates that the average stress in the gel due to shrinkage is not high enough to cause cavitation.

To produce the slab structures, the liquid mixture is injected between the closely spaced plates which have been sealed along two sides. In many instances the liquid mixture can be injected simply by immersing one open end of the two spaced plates in a reservoir of the liquid, and the liquid will rise between the plates as a result of capillary action. For plates spaced apart by 100 microns, capillary action is calculated to cause the liquid to rise by about 15 cm., sufficient for most thin slab gel structures. The heating and pulling apparatus is adapted to handle the slab structures instead of round capillaries. Slabs with heat sensitive mixtures are passed through a linear heat zone, which can be provided by a heating lamp or wire as the linear heater. Slabs with photosensitive mixtures are passed through exposure zones that illuminate the full width of the slab.

It will be apparent to those skilled in the art that there are a large number of changes that may be made without departing substantially from the spirit and scope of the invention. For example, a very broad variety of chemical mixtures may be used to provide a liquid that can be induced to gel at a moving front by the application of energy at that front. The structure and detail of apparatus in the invention may vary as well. There are, for example, many ways to construct a useful cold chamber or dark chamber, and there are many ways of adding energy to initiate and influence gellation. Heat can be provided by such things as lasers, electron beams, other particle beams, electrical resistance, and high intensity infrared lights are examples. Also, ionizing radiation could be used directly, since it can be used to create cations in the mixture that can dissociate to form free radicals. Also, energy may be added by ion beams, and by other frequencies of electromagnetic radiation, such as microwaves, and in other ways, eg. the ambient room temperature may be adequate for activation. Pulling devices for capillaries and plate structures and other gel support structures may be built in a wide variety of ways. All of these variations and others that will be apparent to those skilled in the art are considered within the scope and spirit of the invention as outlined in the appended claims.

What is claimed is:

1. A method of casting a gel in a rigid confined support structure for containing the gel, said support structure having at least one wall constructed of a material that transmits energy, comprising:

coating the wall of said rigid confined support structure with an adhesion enhancing coating for firmly adhering said gel to the wall;

filling said support structure with a mixture containing a gelling material that is promoted to gel by absorption of energy, said material shrinking as it gels, said support structure filled such that said material is continuous from a first location on said wall to a second location on said wall;

providing energy by means of an energy source to a localized area of said wall;

causing relative motion of said support structure and said energy source so that said localized area that receives energy from said source is moved along said wall in a direction from the first location toward the second location on said wall, thereby causing gellation to occur in said gelling mixture and adhesion of the gel to the support structure in a moving zone substantially adjacent to said localized area as said localized area moves, producing in the entire confined support structure a continuous gel substantially free of voids and air bubbles in the absence of degassing.

2. The method of claim 1 wherein said energy source is a heater and wherein said mixture is promoted to gel by heating.

3. The method of claim 2 further comprising the step of cooling those portions of said rigid confined support structure containing said mixture that are located between said moving zone and said second location during said relative motion of said energy source and said rigid confined support structure.

4. The method of claim 1 wherein the adhesion enhancing coating is MAPTMS and wherein the step of coating the wall comprises heating said support structure to cause binding of said MAPTMS to said wall before said mixture is introduced into said rigid confined support structure.

5. The method of claim 1 wherein said rigid confined support structure comprises a capillary tube.

6. The method of claim 1 wherein said wall that transmits energy is flat and wherein said rigid confined support structure further comprises a second flat wall spaced apart from said transmitting wall by spacers and sealed thereto to provide a volume for containing said mixture.

7. The method of claim 6 comprising the step of coating both walls of said rigid confined support structure with an adhesion enhancing coating for increasing adhesion of said gel to said walls.

8. The method of claim 7 wherein the adhesion enhancing coating is MAPTMS and wherein the step of coating the wall comprises heating said walls to cause binding of said MAPTMS to said walls before said mixture is introduced into said rigid confined support structure.

9. The method of claim 1 further comprising the step of applying pressure to the mixture near said second location on said wall to cause flow of said mixture toward said moving zone.

* * * * *